United States Patent [19]

Cuddihy et al.

[11] Patent Number: 4,957,012
[45] Date of Patent: Sep. 18, 1990

[54] PREDICTIVE AGING OF POLYMERS

[75] Inventors: Edward F. Cuddihy, Tujunga; Paul B. Willis, La Canada, both of

[73] Assignee: The United States of America as represented by the Administrator of the National Aeronautics and Space Administration, Washington, D.C.

[21] Appl. No.: 366,957

[22] Filed: Jun. 16, 1989

[51] Int. Cl.$^5$ .................... G01N 21/00; G01N 25/00
[52] U.S. Cl. ................................. 73/866; 219/502; 250/372; 374/53
[58] Field of Search .................... 374/45, 5, 7, 134, 53; 73/865.6, 866; 250/372; 219/502

[56] References Cited

U.S. PATENT DOCUMENTS

| | | |
|---|---|---|
| 2,563,875 | 8/1951 | Saiton . |
| 2,780,708 | 2/1957 | Glynn et al. . |
| 3,697,728 | 10/1972 | Stirzenbecher . |
| 3,698,234 | 10/1972 | Allinikov ................................ 374/5 |
| 3,753,952 | 8/1973 | Guillet et al. . |
| 3,825,626 | 7/1974 | McGaugh et al. . |
| 3,865,767 | 2/1975 | Boberg . |
| 3,886,683 | 6/1975 | Hudgin et al. . |
| 4,544,995 | 10/1985 | Suga ................................ 73/865.6 X |
| 4,725,710 | 2/1988 | Ramus et al. . |
| 4,733,057 | 3/1988 | Stanzel et al. . |
| 4,760,748 | 8/1988 | Katayanagi et al. ............. 374/57 X |
| 4,817,447 | 4/1989 | Kashima et al. .................... 73/865.6 |

Primary Examiner—Daniel M. Yasich
Attorney, Agent, or Firm—Thomas H. Jones; John R. Manning

[57] ABSTRACT

A method of predicting aging of polymers operates by heating a polymer in the outdoors to an elevated temperature until a change of property is induced. The test is conducted at a plurality of temperatures to establish a linear Arrhenius plot which is extrapolated to predict the induction period for failure of the polymer at ambient temperature. An Outdoor Photo Thermal Aging Reactor (OPTAR) is also described including a heatable platen for receiving a sheet of polymer, means to heat the platen and switching means such as a photoelectric switch for turning off the heater during dark periods.

20 Claims, 3 Drawing Sheets

PREDICTIVE AGING OF POLYMERS

ORIGIN OF THE INVENTION

The invention described herein was made in the performance of work under a NASA contract, and is subject to the provisions of Public Law 96-517 (35 USC 202) in which the Contractor has elected not to retain title.

TECHNICAL FIELD

The present invention relates to the degradation of polymers and, more particularly, this invention relates to the accelerated aging of polymers for predicting the outdoor service life of polymers.

BACKGROUND OF THE INVENTION

In the past few decades our society's increasing demands for energy have naturally resulted in increased utilization of renewable resources such as solar energy. One of the most common techniques of directly tapping solar energy involves the use of photovoltaic devices such as silicon solar cells. In general, solar cells are deployed in large solar arrays including numerous solar cells which are intricately positioned and interconnected to provide optimum electricity production.

A common problem in the use of solar cells is the requirement that they be protected from the terrestrial elements over a prolonged period of time. For example, in order to be commercially successful, solar arrays must be suitably encapsulated to achieve at least a 20-year lifetime expectancy in terrestrial environments. This has resulted in a concerted effort to develop a suitable encapsulating material to protect solar arrays from the elements over a sustained period of time.

Polymer films have been a natural choice as possible solar cell encapsulants. However, it has been a most difficult technical problem to develop proper polymers for encapsulating the solar cell arrays to protect the optically and electrically active elements from the degrading effects of typical terrestrial environments. In general, solar cell encapsulants have included three layers—the pottant, an adhesive and a weather resistant layer. The layer directly surrounding the solar cell is known as the pottant. The pottant insulates and protects the delicate mechanical and electrical elements of the solar cell against vibrations resulting from wind, earthquakes and other possible external forces. The adhesive layer is necessary in order to secure the hard outer weather resistant layer to the relatively soft shock proof pottant layer. The weather resistant layer may be composed of different materials such as a hard acrylic polymer on the top and bottom surfaces and black or silicon rubber as a sealant along the edges. This layer functions to protect the solar cell from rain, dust and other debris.

Plastics are finding increasing use in construction as decorative panels, protective films, clear panels and are increasingly being used in air and land vehicles. Many of these plastics degrade due to ultraviolet and infrared components of solar radiation, wind, rain and thermal cycling they are exposed to in the terrestrial environment.

In order to evaluate plastics for suitability for long term use, aging tests have been developed. Indoor tests use artificial light which does not accurately reproduce solar radiation. Laboratory tests are absent the effect of wind and rain and do not utilize light and dark cycling as experienced in an outdoor environment. Outdoor tests in which a panel of plastic is mounted in a fixture facing the sun do subject the sample of panel to realistic environmental conditions. However, it requires very long test periods to reach induction of a change of property such as elongation failure.

STATEMENT OF THE INVENTION

A method of accelerating the aging of polymers is provided in accordance with the invention. The method accurately predicts the outdoor service life of polymers. The plastic part is placed in the outdoor environment during the test under realistically accelerated conditions. Natural sunlight is used as the light source, thus avoiding the unpredictable effect of unnatural, artificial light sources. Furthermore, a natural light source is free, not subject to failure and unpredictable periodic replacement. All other environmental elements, such as rainfall and wind are included in the test. The outdoor environment also includes the effect of light-dark exposure experienced by any polymer in outdoor service. The method permits accurate prediction of outdoor polymer service life from measurement of induction periods to a change in a property of the polymer under realistically accelerated service conditions.

The method of the invention is based on the discovery that heat is the accelerator, but not the initiator of photothermal degradation reactions. Aging is, therefore, accomplished by the addition of heat and natural sunlight, which is much more spectrally consistent than artificial sources. Dark cycles' reactions are also included, as are the other elements of weathering, such as moisture, wind and rainfall. The only accelerating stress is temperature, the other environmental conditions being present in their natural occurrence and intensity.

The predictive capability of this type of aging may be based on simple first-order behavior, in which the log of particular property is found to be linear over time. Polymers frequently depart from this type of behavior, however, and show "induction period" behavior in which a property changes suddenly after a period of time. It has been found that the log of the induction period (for these polymers) is linear when plotted against the reciprocal absolute temperature (Arrhenius relationship).

This observation now permits heat to be used as a controllable variable in the accurate acceleration of photothermal degradation reactions. Extrapolation from high temperatures to ambient temperatures permits the induction period of polymer failure to be calculated with accuracy. This reveals the actual lifetime of the plastic part in outdoor service.

The invention also relates to an Outdoor, Photo-Thermal Aging Reactor (OPTAR) device. The device is designed to contain sealed components suitable for outdoor usage. The OPTAR includes a thermal platen assembly such as an aluminum sheet faced with a sheet of stainless steel and backed with silicone heaters. A thermocouple is mounted on the side of the platen. The platen assembly is mounted in a caulked, wooden frame and the frame is hinged so that it can be angled to face the sun. A controller controls temperature and a timer or light activated switch can be utilized to switch the heaters on only during daylight hours.

The OPTAR device is easily constructed from readily available materials. The OPTAR does not require periodic replacement of bulbs and the solar light source avoids the anomalies of failed light sources and the error of unnatural light source. The test method of the invention is comparatively inexpensive and requires little maintenance while providing accelerated aging of polymers in a manner accurately predicting real time induction of property change.

STATEMENT OF THE PRIOR ART

I. Patents relating to the Testing Method.

| PATENT NO. | ISSUED | PATENTEE |
|---|---|---|
| 3,753,952 | 8/21/73 | Guillet et.al. |
| 3,825,626 | 7/23/74 | McGaugh et.al. |
| 3,865,767 | 2/11/75 | Boberg |
| 3,886,683 | 6/03/75 | Hudgin et.al. |

The first group of patents relate to testing of polymers intended to photodegrade in the environment—the opposite characteristic desired in solar cell encapsulating films for which the OPTAR was designed. These patents disclose either outdoor solar aging experiments or indoor accelerated U.V. testing. The patents recognize the contribution of heat as an accelerator but not an initiator of photo-actinic degradative aging. The most relevant patent is Hudgin et al who at Column 13 disclose photothermal degradation and the construction of a wooden frame for holding samples of polymer in the outdoors. The ambient temperature is closely monitored. None of the patents disclose heating a polymer sheet while it is exposed to sunlight.

II. Patents Relating to the Sheet Heating Devices

| PATENT NO. | ISSUED | PATENTEE |
|---|---|---|
| 2,563,875 | 08/14/51 | Salton |
| 2,780,708 | 02/05/57 | Glynn et.al. |
| 3,697,728 | 10/10/72 | Stirzenbecher |
| 4,725,710 | 02/16/88 | Ramus et.al. |
| 4,733,057 | 03/22/88 | Stanzel et.al. |

The collected patents disclose strip heaters secured to the rear surface of a substrate. However, these patents do not disclose any device having sheet clamping means and a hinged frame for exposing the sheet to the sun. The patents also do not show timer-controllers or optical switches for turning on the heaters during periods of sunlight.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
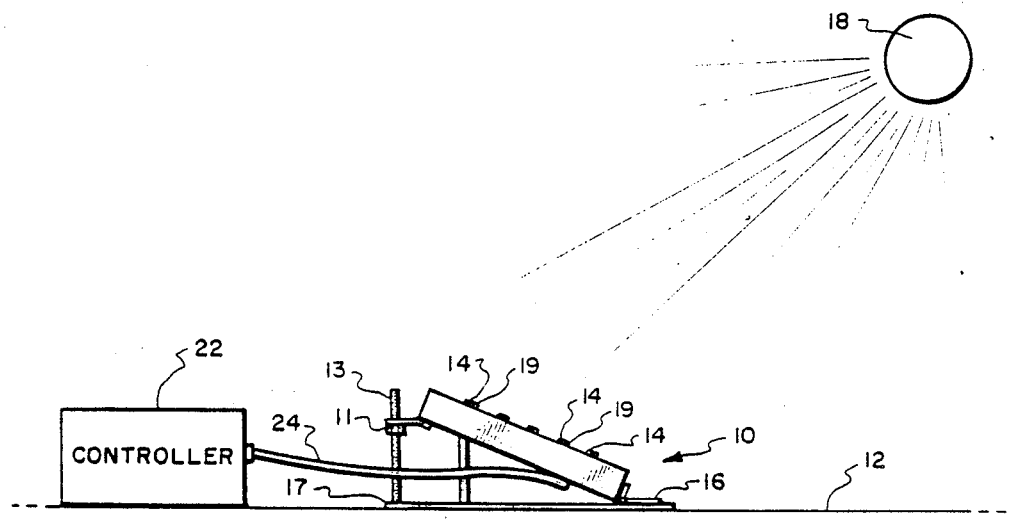
FIG. 1 is a side view in elevation of the heated platen assembly.
Figure 2:
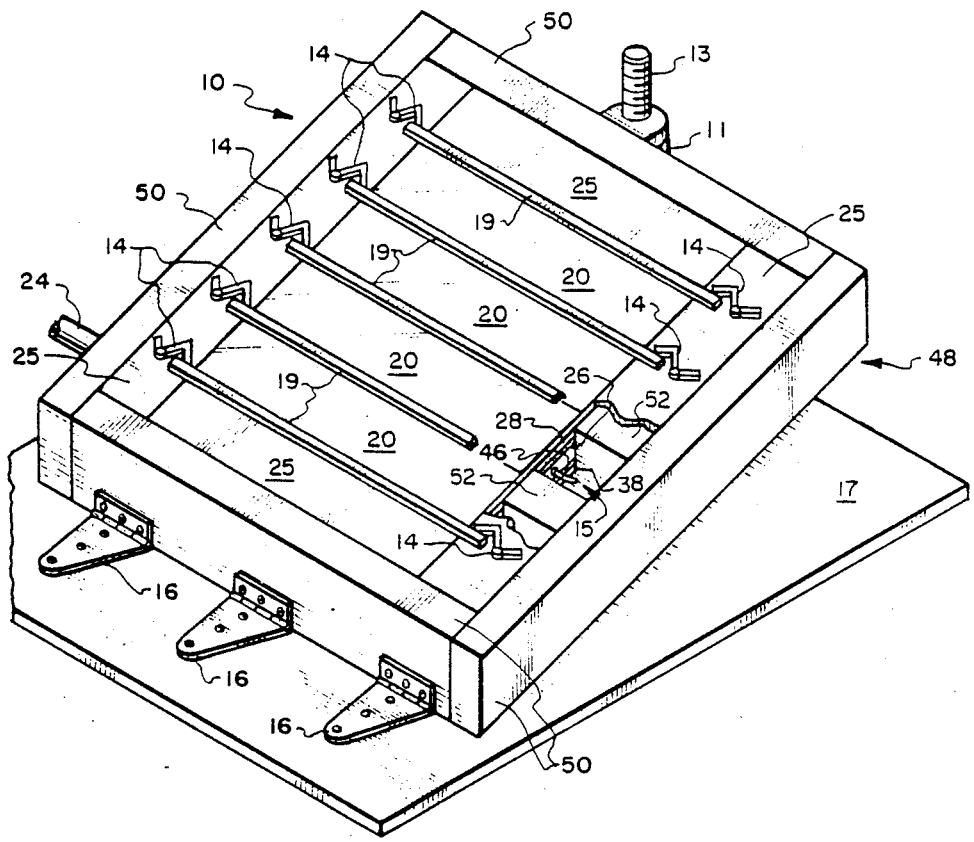
FIG. 2 is an isometric view of the OPTAR ractor showing the strip heaters partially broken away to expose the platen and thermocouple.
Figure 3:
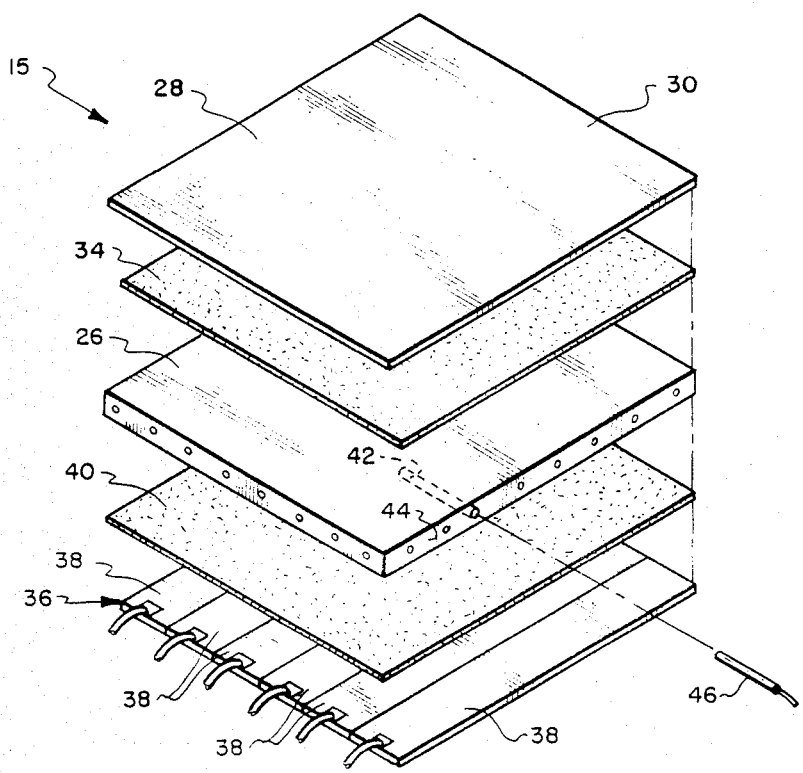
FIG. 3 is an exploded isometric view of the platen assembly.

Referring now to FIGS. 1 through 4, the OPTAR device 10 is shown placed on the ground 12 in an outdoor environment with the hinges 16 angled about 45° South to face the device 10 toward the prevalent direction of the sun 18. The elevation of the device 10 is adjusted by means of a latitude adjustment screw 13 received through a threaded flange 11 attached to a frame member 50. The bottom edge of the screw 13 bears against a plate 17. The hinges 16 are also attached to the plate 17. Strips of plastic 20, are mounted on the front surface of the OPTAR device 10 by means of changing bars 19 held by releasable clamps 14, such as De-Sta-Co. clamps, which flush mount the sheet on the surface of a plate 28. The OPTAR device 10 is connected to a controller 22 by a lead 24.

The heated platen assembly 15 is formed of a thick block 26 of a material having high heat capacity and conductivity such as a half-inch thick block of aluminum. The block 26 can have any shape, suitably a rectangle or square having a side dimension between 1 and 5 feet, preferably a 3 foot square sheet of material. The block 26 may be faced with a smooth mounting plate 28 such as a sheet of 16 gauge 3 or 4 stainless steel, 60 mil. thick having a polished front surface 30. The mounting plate or sheet 28 may be secured to the heating block 26 by means of a layer 34 of adhesive suitably a silicone adhesive such as RTV 116. A heater 36 is applied to the rear surface of the block 26 in order to provide better thermal management of the block. It is preferred to use a plurality of strip heaters 38 each of which is applied to the surface of the block by a suitable environmentally resistant adhesive such as a layer 40 of silicone adhesive such as RTV 116. A thermocouple well 42 may be provided in one end edge 44 of the block 26. The well receives a thermocouple 46.

The heated platen assembly 15 is mounted in a rack 48 suitably formed of edge framing members 50 connected by cross brace members 52. The cross members may be indented by the thickness of the heated platen assembly 15. The outer edges of the cross members are faced with thin facing strips 25 in order to form a cavity or well for receiving the test strips 20 flush with the top surface of the facing strips 25. The frame members and facing strip should be kiln dried and painted with an environmentally resistant coating in order to be able to withstand the effects of long term usage in the environment.

Figure 4:
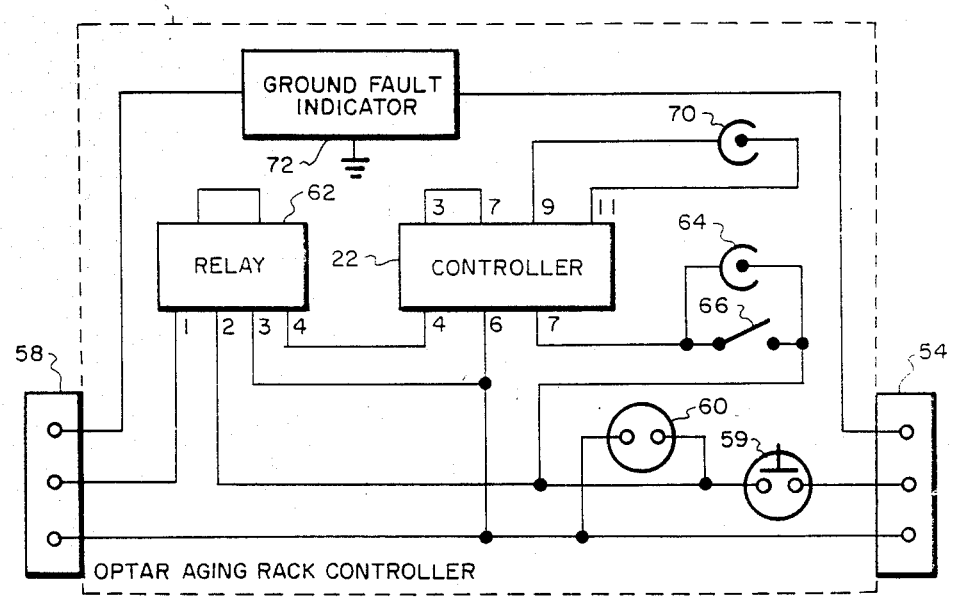
FIG. 4 is an electronic block diagram of the OPTAR aging rack controller.

Referring now to FIG. 4, OPTAR aging rack controller 21, the device 10 is operated by the controller 22 which turns the heaters on at sunrise and turns them off at sun down and controls the temperature to a pre-set temperature by means of signal generated by means of a thermocouple 46. The controller 22 has a terminal 54 for connecting the heat controlling unit to 120 volt power and a connector 58 receiving the signal wire from the thermocouple 36 and for sending power to the strip heaters. The controller unit may also contain a circuit breaker 59 indicator light 60 and a relay 62 for switching on the strip heaters 38 in order to operate the controller in cold-dark cycles and heated-light cycles. The controller contains a photoswitch 64. Optionally, the unit may be operated by a clock to operate within dark and light cycles. A photoswitch bypass 66 may be provided when a timer is used for when it is desired to operate or test the device. A thermocouple connector 70 is connected to the controller 22. A ground fault indicator circuit 72 may optionally be provided.

The device is operated by calibrating the device so that the desired surface temperature is achieved and verified. A sheet of specimen polymer is then clamped so that the measurement areas are flush with the heated surface and exposed to sunlight. Test specimens are removed at known intervals and their properties determined as a function of time at a plurality of temperatures sufficient to establish an Arrhenius plot. This straight line plot can be extrapolated to predict time and failure at normal ambient temperature.

Figure 5:
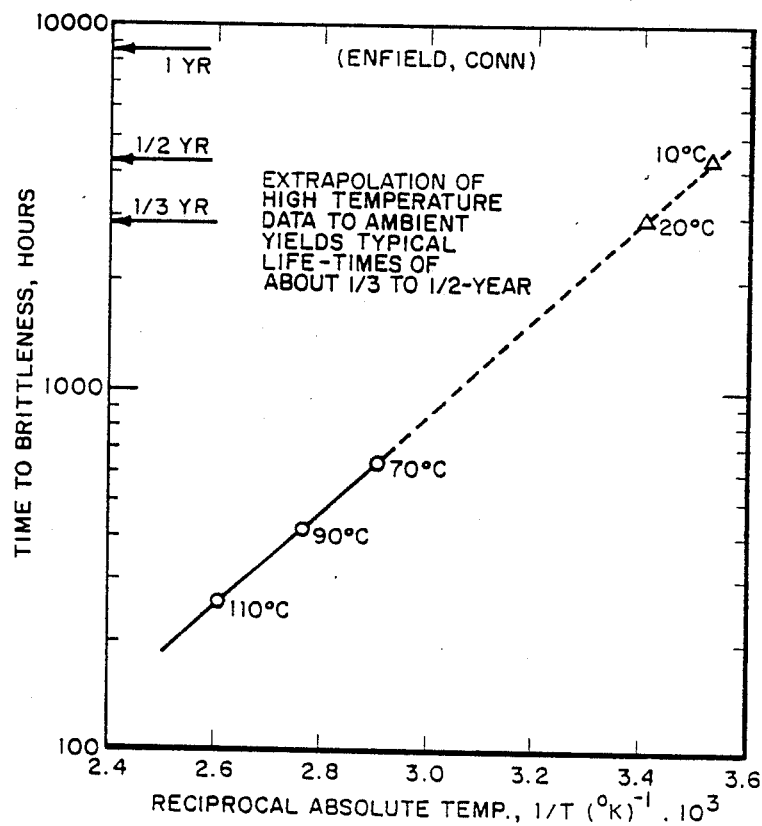
FIG. 5 is an illustrative curve representing the natural outdoor aging pattern for unstabilized polypropylene.

The first experiments were conducted on sheets of unstabilized polypropylene. FIG. 5 is an illustrative representation of the natural outdoor aging pattern for unstabilized polypropylene. It is a plot of elongation at break versus aging time outdoors. The aging is characterized by two stages: an initial induction period during with the elongation at break is virtually unchanged, followed by second stage that is an almost precipitous drop in elongation. This second stage reflects brittle failure of the polypropylene sample and the time associated with the onset of this precipitous drop in the time-to-brittleness, which is a function of temperature.

Figure 6:
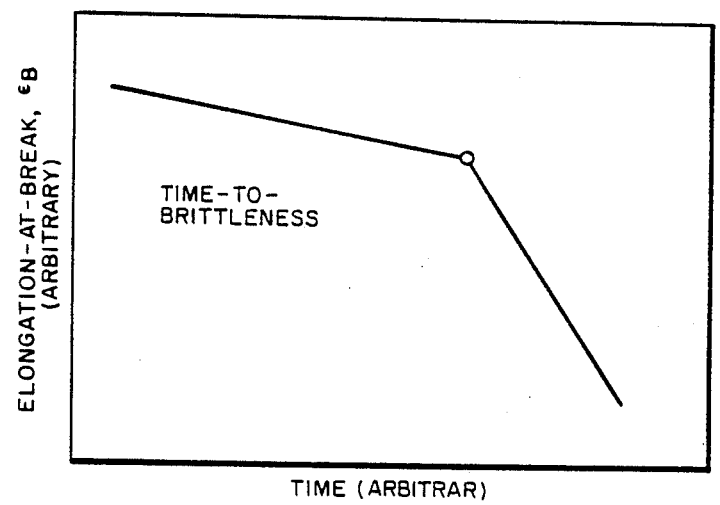
FIG. 6 is an Arrehenius plot of log time-to-failure versus 1/K for unstabilized polypropylene.

Tensile bars of unstabilized compression-molded polypropylene were placed on the OPTAR device at three temperatures and aged until brittle. FIG. 6 is an Arrhenius plot of the time-to-brittleness at each of the OPTAR temperatures. Extrapolation of the data line to lower air temperatures predicts the known outdoor aging time of the polypropylene at ambient conditions. A correlation coefficient of 0.97 indicates the very high accuracy of the method.

The OPTAR device of the invention has also been used to test under accelerated aging conditions other polymers such as ethylene vinyl acetate (EVA), polyurethane, polyvinylbenzimidazole and ethyl methacrylate (EMA). The OPTAR device and method of the invention generates aging date in the shortest times yet observed. In the case of the EVA materials induction to change of tensile and modulus occurred at about 6,000 hours. For EMA induction occurred at about 5,000 hours. For polyurethane induction occurred at about 1,000 hours.

The aging method of the invention eliminate the difficulties associated with irregular spectrum of artificial light sources, exposes the specimen to other environmental conditions such as rain and pollution and additionally incorporates a dark cycle. Many chemical reactions occur during the dark cycle which effect physical properties. The only acceleration is from the elevated temperature, all other environmental conditions being present in their natural occurrence and intensity. In summary the OPTAR device is considered to have the following advantages:

(1) Uses natural sunlight, therefore, avoids the spectrum distribution problems encountered with artificial light sources.
(2) Uses temperature to accelerate the photothermal reactions and is easily controllable.
(3) Includes dark-cycle reactions that are a natural part of field exposure.
(4) Includes dew and rain water extraction effects.
(5) More closely resembles the environmental conditions experienced by solar modules.
(6) Easily accommodates both discrete materials and OPTAR modules.
(7) May be set at any temperature desired for the purpose of varying the acceleration rate or extrapolating to lower temperatures.

It is to be realized that only preferred embodiments of the invention have been described and that numerous substitutions, modifications and alterations are permissible without departing from the spirit and scope of the invention as defined in the following claims.

We claim:

1. A method of predicting the aging of polymers exposed to solar radiation in the outdoors comprising the steps of:
   (a) Placing a specimen of a polymers to be tested on a heatable platen assembly;
   (b) Disposing the platen assembly in an outdoor environment during periods of sunlight alternating with periods of dark such that the polymer specimen is exposed to and receives solar radiation from the sun during periods of sunlight;
   (c) Periodically heating the platen assembly only during said periods of sunlight to a constant temperature from between 30° C. up to 20° C. below the melting temperature of the polymer being tested to periodically heat the polymer specimen while it is exposed to sunlight;
   (d) Measuring a physical property of the polymer specimen over an induction period from the initial disposition of the polymer specimen outdoors until a sudden change in said physical property; and
   (e) recording said induction period.

2. A method according to claim 1 in which the temperature is from 50° C. to 150° C.

3. A method according to claim 2 in which the steps of (a) to (e) are repeated on said polymer specimens at two different temperatures.

4. A method according to claim 3 further including the step of extrapolating the relationship of the induction periods at the different temperatures to ambient temperature to predict the induction period of said polymers at ambient temperature.

5. A method according to claim 1 in which the platen assembly is mounted at an angle from 30° to 60° to the ground.

6. A method according to claim 5 in which the platen assembly is slanted at an angle of 45° to the ground.

7. A method according to claim 6 in which the platen assembly includes a block of high heat capacity metal.

8. A method according to claim 7 in which the front surface of the platen assembly is faced with a plate of polished metal.

9. A method according to claim 8 in which the block comprises aluminum and the plate comprises stainless steel.

10. A method according to claim 9 in which a heating means is attached to the rear surface of the plate.

11. A method according to claim 10 in which the heating means comprises a plurality of strip heaters attached to said rear surface.

12. A method according to claim 11 further including the steps of attaching to the block a temperature control sensor which develops a temperature control signal, and controllably providing power to the heating means by means of a power supply receiving the signal from the sensor and thereby controlling the temperature of the platen assembly.

13. A method according to claim 12 in which the power supply includes switch means for selectively turning the means off during dark periods.

14. An outdoor photothermal aging reactor for the predictive aging of polymers comprising:
 (a) a heatable platen assembly having edges and having a front surface for receiving a specimen of polymer to be tested and having a rear surface;
 (b) heating means attached to the rear surface of the platen assembly for heating the assembly and polymer specimen;
 (c) a temperature sensor applied to the platen assembly for developing a signal indicative of the temperature of the platen assembly;
 (d) a controller receiving the signal from said sensor and connected to the heating means for maintaining the temperature of the platen assembly at a constant temperature; and
 (e) stand means for disposing the front surface of the platen assembly in a preselected direction and at a preselected angle.

15. A reactor according to claim 14 further including a frame attached to the edges of the platen assembly.

16. A reactor according to claim 15 further including light-activated switch means in said controller for automatically turning off the heating means during dark periods.

17. A reactor according to claim 16 in which the switch means comprises a photoelectric sensor.

18. A reactor according to claim 17 in which the platen assembly comprises a thick block of high heat capacity metal having a front surface and a rear surface and having a well, the heating means comprises a plurality of strip heaters attached to the rear surface of the block and the temperature sensor comprises a thermostat received in the well in the block.

19. A reactor according to claim 18 further including a plate of polished metal attached to the front surface of the block.

20. A reactor according to claim 19 in which the body comprises aluminum and the plate comprises stainless steel.

* * * * *